United States Patent
Nishi et al.

(10) Patent No.: US 11,285,139 B2
(45) Date of Patent: Mar. 29, 2022

(54) TREATMENT OF CNS CONDITIONS

(71) Applicant: Takeda Pharmaceutical Company Limited, Osaka (JP)

(72) Inventors: Toshiya Nishi, Cambridge, MA (US); Shinichi Kondo, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 98 days.

(21) Appl. No.: 16/642,153

(22) PCT Filed: Aug. 30, 2018

(86) PCT No.: PCT/JP2018/032949
§ 371 (c)(1),
(2) Date: Feb. 26, 2020

(87) PCT Pub. No.: WO2019/045121
PCT Pub. Date: Mar. 7, 2019

(65) Prior Publication Data
US 2020/0306238 A1 Oct. 1, 2020

Related U.S. Application Data

(60) Provisional application No. 62/553,070, filed on Aug. 31, 2017.

(51) Int. Cl.
*A61K 31/4545* (2006.01)
*A61P 25/08* (2006.01)
*A61K 45/06* (2006.01)

(52) U.S. Cl.
CPC .......... *A61K 31/4545* (2013.01); *A61P 25/08* (2018.01); *A61K 45/06* (2013.01)

(58) Field of Classification Search
CPC .. A61K 31/444; A61K 31/4545; A61K 45/06; A61P 25/08
See application file for complete search history.

(56) References Cited

U.S. PATENT DOCUMENTS

| | | |
|---|---|---|
| 8,648,079 B2 | 2/2014 | Koike et al. |
| 8,865,717 B2 | 10/2014 | Koike et al. |
| 8,871,766 B2 | 10/2014 | Koike et al. |
| 9,193,709 B2 | 11/2015 | Koike et al. |
| 9,440,990 B2 | 9/2016 | Koike et al. |
| 9,586,930 B2 | 3/2017 | Koike et al. |
| 10,144,743 B2 | 12/2018 | Koike et al. |
| 10,273,245 B2 | 4/2019 | Koike et al. |
| 10,550,129 B2 | 2/2020 | Koike et al. |
| 10,562,881 B2 | 2/2020 | Komura et al. |
| 2013/0090341 A1 | 4/2013 | Koike et al. |
| 2014/0088118 A1 | 3/2014 | Koike et al. |
| 2014/0088146 A1 | 3/2014 | Koike et al. |
| 2014/0228373 A1 | 8/2014 | Koike et al. |
| 2015/0376205 A1 | 12/2015 | Koike et al. |
| 2016/0326136 A1 | 11/2016 | Koike et al. |
| 2017/0145031 A1 | 5/2017 | Koike et al. |
| 2018/0297980 A1 | 10/2018 | Komura et al. |
| 2019/0071455 A1 | 3/2019 | Koike et al. |
| 2019/0233436 A1 | 8/2019 | Koike et al. |

OTHER PUBLICATIONS

Auvin et al., Neurobiol. Dis., publ. Mar. 16, 2016, vol. 92, pp. 72-89 (Year: 2016).*
Shao et al. Seminar. Ped. Neurol., vol. 23, pp. 98-107, publ. 2016 (Year: 2016).*
Vigevano et al., Epilepsia, vol. 54(suppl 8), pp. 45-50, publ. 2013 (Year: 2013).*
Von Deimling et al., "Epileptic Encephalopathies—Clinical Syndromes and Pathophysiological Concepts," Curr. Neurol. Neurosci. Rep., Feb. 22, 2017, 17(2):1-10.

* cited by examiner

*Primary Examiner* — Sarah Pihonak
(74) *Attorney, Agent, or Firm* — Honigman LLP; Lucy X. Yang; Jonathan P. O'Brien

(57) ABSTRACT

Aspects of the present invention relate to a method of treating an epileptic encephalopathy in a mammal in need thereof, comprising administering a composition comprising an effective amount of (4-benzyl-4-hydroxypiperidin-1-yl) (2,4'-bipyridin-3-yl)methanone or a pharmaceutically acceptable salt thereof to the mammal.

25 Claims, No Drawings

TREATMENT OF CNS CONDITIONS

CROSS-REFERENCE TO RELATED APPLICATIONS

This application is the U.S. National Stage of PCT/JP2018/032949, filed Aug. 30, 2018, which claims benefit priority of U.S. Provisional Application No. 62/553,070 filed on Aug. 31, 2017.

TECHNICAL FIELD

The present invention relates to a method of treating an epileptic encephalopathy in a mammal in need thereof, comprising administering a composition comprising an effective amount of (4-benzyl-4-hydroxypiperidin-1-yl) (2,4'-bipyridin-3-yl)methanone or a pharmaceutically acceptable salt thereof to the mammal.

BACKGROUND OF THE INVENTION

The term epileptic encephalopathies describes a heterogeneous group of epilepsy syndromes in which the epileptic activity itself may contribute to severe cognitive and behavioral impairments above and beyond what might be expected from the underlying pathology alone (e.g., cortical malformation) and that can worsen over time. These disorders are generally diagnosed in childhood and adolescence, varying in their etiologies, seizure types, electroencephalographic patterns, cognitive deficits, and prognosis, while sharing a consistent and significant impact on neurological development.

Patent document 1 describes the compound, (4-benzyl-4-hydroxypiperidin-1-yl) (2,4'-bipyridin-3-yl)methanone, having a superior CH24H inhibitory action shown below as Formula (I):

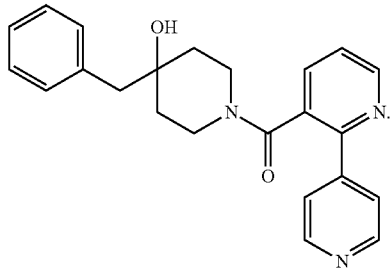

Formula (I)

DOCUMENT LIST

Patent Document

[Patent Document 1] U.S. Pat. No. 8,648,079

SUMMARY OF THE INVENTION

Problems to be Solved by the Invention

An object of the present invention is to provide a superior method of treating an epileptic encephalopathy in a mammal in need thereof, comprising administering a composition comprising an effective amount of (4-benzyl-4-hydroxypiperidin-1-yl) (2,4'-bipyridin-3-yl)methanone or a pharmaceutically acceptable salt thereof to the mammal.

Means of Solving the Problems

The present inventors have conducted intensive studies in an attempt to solve the above-mentioned problem and found that a novel method of treating an epileptic encephalopathy in a mammal in need thereof, comprising administering a composition comprising an effective amount of (4-benzyl-4-hydroxypiperidin-1-yl) (2,4'-bipyridin-3-yl)methanone or a pharmaceutically acceptable salt thereof to the mammal, which resulted in the completion of the present invention.

Accordingly, the present invention provides the following:

[1] A method of treating an epileptic encephalopathy in a mammal in need thereof, comprising administering a composition comprising an effective amount of (4-benzyl-4-hydroxypiperidin-1-yl) (2,4'-bipyridin-3-yl)methanone or a pharmaceutically acceptable salt thereof to the mammal.

[2] The method of the above-mentioned [1], wherein the epileptic encephalopathy is selected from the group of Dravet syndrome (DS), Early myoclonic encephalopathy, Epilepsy with continuous spike-and-waves during slow-wave sleep (other than Landau-Kleffner syndrome), epilepsy of infancy with migrating focal seizures, Hypothalamic epilepsy, Landau-Kleffner syndrome, Lennox-Gastaut syndrome (LGS), Doose syndrome (myoclonic-astatic epilepsy), Myoclonic status in non-progressive encephalopathies, Ohtahara syndrome or early infantile epileptic encephalopathy, West syndrome, Glycine encephalopathy, 15q duplication syndrome (Dup 15q) and Tuberous Sclerosis Complex (TSC) and seizures associated with mutations in CHD2, Cyclin-Dependent Kinase-Like 5 (CDKL5), SCN1A, SCN2A, SCN8A, ARX, KCNA1, KCNA2, KCNT1, KCNQ2, HCN1, PCDH19, GRIN1, GRIN2A and GRIN2B.

[3] The method of the above-mentioned [1], wherein the epileptic encephalopathy is selected from the group of Dravet syndrome (DS), Lennox-Gastaut syndrome (LGS), Tuberous Sclerosis Complex (TSC) and seizures associated with mutations in CHD2, Cyclin-Dependent Kinase-Like 5 (CDKL5), SCN1A, SCN2A, SCN8A, ARX, KCNA1, KCNA2, KCNT1, KCNQ2, HCN1, PCDH19, GRIN1, GRIN2A and GRIN2B.

[4] The method of any of the above-mentioned [1] to [3], wherein administering the effective amount of (4-benzyl-4-hydroxypiperidin-1-yl) (2,4'-bipyridin-3-yl)methanone or a pharmaceutically acceptable salt thereof results in (i) a reduction in the frequency of seizures in the mammal and/or (ii) a reduction in the plasma 24HC levels in the mammal.

[5] The method of any of the above-mentioned [1] to [4], wherein the effective amount of (4-benzyl-4-hydroxypiperidin-1-yl) (2,4'-bipyridin-3-yl)methanone or a pharmaceutically acceptable salt thereof is administered orally.

[6] The method of any of the above-mentioned [1] to [5], wherein the effective amount of (4-benzyl-4-hydroxypiperidin-1-yl) (2,4'-bipyridin-3-yl)methanone or a pharmaceutically acceptable salt thereof is administered as a single unit dose.

[7] The method of the above-mentioned [6], wherein the single unit dose is at least about 0.8 mg/kg.

[8] The method of the above-mentioned [6] or [7], wherein the single unit dose is between about 2 mg/kg and about 12 mg/kg.

[9] The method of any of the above-mentioned [6] to [8], wherein the single unit dose is selected from the consisting of about 0.8 mg/kg, about 2 mg/kg, about 3 mg/kg, about 3.33 mg/kg, about 4 mg/kg, about 5 mg/kg, about 6 mg/kg, about 10 mg/kg, and about 12 mg/kg.

[10] The method of any of the above-mentioned [1] to [9], wherein the effective amount of (4-benzyl-4-hydroxypiperidin-1-yl) (2,4'-bipyridin-3-yl)methanone or a pharmaceutically acceptable salt thereof is administered according to a dose regimen of either twice a day (BID) or once a day (QD) dosing.

[11] The method of any of the above-mentioned [1] to [10], wherein the mammal is a human.

[12] The method of the above-mentioned [11], wherein the human is an adult (18 years old or older), a juvenile (between 12 and 17 years old, endpoint inclusive), a child (between 2 and 11 years old, endpoint inclusive), an infant (between 1 month and 1 year of age, endpoint inclusive).

[13] The method of the above-mentioned [11] or [12], wherein the effective amount of (4-benzyl-4-hydroxypiperidin-1-yl) (2,4'-bipyridin-3-yl)methanone or a pharmaceutically acceptable salt thereof is administered as a single unit dose.

[14] The method of the above-mentioned [13], wherein the single unit dose is less than about 1350 mg.

[15] The method of the above-mentioned [13] or [14], wherein the single unit dose is between about 50 mg and about 800 mg.

[16] The method of any of the above-mentioned [13] to [15], wherein the single unit dose is between about 100 mg and about 800 mg.

[17] The method of any of the above-mentioned [13] to [16], wherein the single unit dose is selected from the group consisting of about 100 mg, about 150 mg, about 200 mg, about 300 mg, about 400 mg, about 600 mg and about 800 mg.

[18] The method of the above-mentioned [11], wherein the effective amount of (4-benzyl-4-hydroxypiperidin-1-yl) (2,4'-bipyridin-3-yl)methanone or a pharmaceutically acceptable salt thereof is administered twice a day.

[19] The method of the above-mentioned [18], wherein (4-benzyl-4-hydroxypiperidin-1-yl) (2,4'-bipyridin-3-yl)methanone is administered at the daily dose of between about 100 mg and about 800 mg.

[20] The method of the above-mentioned [18] or [19], wherein (4-benzyl-4-hydroxypiperidin-1-yl) (2,4'-bipyridin-3-yl)methanone is administered according to a dose regimen selected from the group consisting of about 50 mg twice a day, about 100 mg twice a day, about 200 mg twice a day, about 300 mg twice a day and about 400 mg twice a day.

[21] The method of any of the above-mentioned [18] to [20], wherein (4-benzyl-4-hydroxypiperidin-1-yl) (2,4'-bipyridin-3-yl)methanone is administered according to a dose regimen of about 400 mg twice a day.

[22] The method of any of the above-mentioned [1] to [21], further comprising administering an additional composition comprising an effective amount of an additional anti-epileptic drug.

[23] The method of the above-mentioned [22], wherein the additional anti-epileptic drug is selected from the group of acetazolamide, brivaracetam, bromide, cannabidiol, carbamazepine, clobazam, clonazepam, diazepam, eslicarbazepine acetate, ethosuximide, felbamate, fosphenytoin sodium, gabapentin, lacosamide, lamotrigine, levetiracetam, lorazepam, mephenytoin, methlyphenobarbital, methosuximide, nitrazepam, oxcarbazepine, perampanel, piracetam, phenobarbital, phenytoin, pregabalin, primidone, retigabine, rufinamide, sodium valproate, stiripentol, tiagabine, topiramate, fenfluramine, vigabatrin, and zonisamide.

[24] The method of any of the above-mentioned [1] to [21], wherein the composition further comprises one or more of an additional anti-epileptic drug and a pharmaceutically acceptable carrier.

[25] The method of the above-mentioned [24], wherein the additional anti-epileptic drug is selected from the group of acetazolamide, brivaracetam, bromide, cannabidiol, carbamazepine, clobazam, clonazepam, diazepam, eslicarbazepine acetate, ethosuximide, felbamate, fosphenytoin sodium, gabapentin, lacosamide, lamotrigine, levetiracetam, lorazepam, mephenytoin, methlyphenobarbital, methosuximide, nitrazepam, oxcarbazepine, perampanel, piracetam, phenobarbital, phenytoin, pregabalin, primidone, retigabine, rufinamide, sodium valproate, stiripentol, tiagabine, topiramate, vigabatrin, and zonisamide.

[26] A pharmaceutical composition comprising (4-benzyl-4-hydroxypiperidin-1-yl) (2,4'-bipyridin-3-yl)methanone or a pharmaceutically acceptable salt thereof, which is for treating an epileptic encephalopathy.

[27] (4-Benzyl-4-hydroxypiperidin-1-yl) (2,4'-bipyridin-3-yl)methanone or a pharmaceutically acceptable salt thereof for use in treatment of epileptic encephalopathy.

Effect of the Invention

A pharmaceutical composition comprising an effective amount of (4-benzyl-4-hydroxypiperidin-1-yl) (2,4'-bipyridin-3-yl)methanone or a pharmaceutically acceptable salt thereof is useful for the prophylaxis or treatment of epileptic encephalopathy. According to the present invention, a superior method of treating an epileptic encephalopathy in a mammal in need thereof, comprising administering a composition comprising an effective amount of (4-benzyl-4-hydroxypiperidin-1-yl) (2,4'-bipyridin-3-yl)methanone or a pharmaceutically acceptable salt thereof to the mammal can be provided.

DETAILED DESCRIPTION OF THE INVENTION

The present invention is explained in detail in the following.

Aspects of the present invention relate to a method of treating an epileptic encephalopathy in a mammal in need thereof, comprising administering a composition comprising an effective amount of (4-benzyl-4-hydroxypiperidin-1-yl) (2,4'-bipyridin-3-yl)methanone or a pharmaceutically acceptable salt thereof to the mammal.

In some embodiments, the epileptic encephalopathy is selected from the group of Dravet syndrome (DS, severe myoclonic epilepsy in infancy), Early myoclonic encephalopathy, Epilepsy with continuous spike-and-waves during slow-wave sleep (other than Landau-Kleffner syndrome), epilepsy of infancy with migrating focal seizures, Hypothalamic (gelastic) epilepsy, Landau-Kleffner syndrome, Lennox-Gastaut syndrome (LGS), Doose syndrome (myoclonic-astatic epilepsy), Myoclonic status in non-progressive encephalopathies, Ohtahara syndrome or early infantile epileptic encephalopathy, West syndrome, Glycine encephalopathy, 15q duplication syndrome (Dup15q) and Tuberous Sclerosis Complex (TSC) and seizures associated with mutations in CHD2, Cyclin-Dependent Kinase-Like 5 (CDKL5), SCN1A, SCN2A, SCN8A, ARX, KCNA1, KCNA2, KCNT1, KCNQ2, HCN1, PCDH19, GRIN1, GRIN2A, GRIN2B, GRIN2D, CACNA1A, GABABRA1, GABRB1, GABRB2, GABRB3, GABRG2, ATP1A2, SLC2A1, SLC6A1, STXBP1 and SYNGAP1.

In some embodiments, the epileptic encephalopathy is selected from the group of Dravet syndrome (DS), Lennox-Gastaut syndrome (LGS), and Tuberous Sclerosis Complex (TSC).

In some embodiments, administering the effective amount of (4-benzyl-4-hydroxypiperidin-1-yl) (2,4'-bipyridin-3-yl)methanone or a pharmaceutically acceptable salt thereof results in (i) a reduction in the frequency of seizures in the mammal and/or (ii) a reduction in the plasma 24HC levels in the mammal.

In some embodiments, the effective amount of (4-benzyl-4-hydroxypiperidin-1-yl) (2,4'-bipyridin-3-yl)methanone or a pharmaceutically acceptable salt thereof is administered orally.

In some embodiments, the effective amount of (4-benzyl-4-hydroxypiperidin-1-yl) (2,4'-bipyridin-3-yl)methanone or a pharmaceutically acceptable salt thereof is administered as a single unit dose, optionally of at least about 0.8 mg/kg, between about 2 mg/kg and about 12 mg/kg, about 2 mg/kg, about 3 mg/kg, about 3.33 mg/kg, about 4 mg/kg, about 5 mg/kg, about 6 mg/kg, about 10 mg/kg, or about 12 mg/kg.

In some embodiments, the effective amount of (4-benzyl-4-hydroxypiperidin-1-yl) (2,4'-bipyridin-3-yl)methanone or a pharmaceutically acceptable salt thereof is administered as a daily dose, between about 50 mg twice a day (BID), about 100 mg BID, about 200 mg BID or about 300 mg BID.

In some embodiments, the effective amount of (4-benzyl-4-hydroxypiperidin-1-yl) (2,4'-bipyridin-3-yl)methanone or a pharmaceutically acceptable salt thereof is administered according to a dose regimen of either twice a day (BID) or once a day (QD) dosing.

In some embodiments, the mammal is a human, optionally, an adult (18 years old or older), a juvenile (between 12 and 17 years old, endpoint inclusive), a child (between 2 and 11 years old, endpoint inclusive), an infant (between 1 month and 1 year of age, endpoint inclusive). In further embodiments, the effective amount of (4-benzyl-4-hydroxypiperidin-1-yl) (2,4'-bipyridin-3-yl)methanone or a pharmaceutically acceptable salt thereof is administered as a single unit dose, optionally of less than about 1350 mg, between about 50 mg and about 800 mg, (preferably between about 100 mg and about 800 mg), about 50 mg, about 100 mg, about 150 mg, about 200 mg, about 300 mg, about 400 mg, about 600 mg or about 800 mg.

In some embodiments, the mammal is a human, optionally, an adult (18 years old or older), a juvenile (between 12 and 17 years old, endpoint inclusive), a child (between 2 and 11 years old, endpoint inclusive), or an infant (between 1 month and 1 year of age, endpoint inclusive). In further embodiments, the effective amount of (4-benzyl-4-hydroxypiperidin-1-yl) (2,4'-bipyridin-3-yl)methanone or a pharmaceutically acceptable salt thereof is administered twice a day, optionally of about 50 mg BID, 100 mg BID, 200 mg BID, 300 mg BID, or 400 mg BID (preferably 300 mg BID or 400 mg BID).

In some embodiments, the method further comprises administering an additional composition comprising an effective amount of an additional anti-epileptic drug, optionally acetazolamide, brivaracetam, bromide, cannabidiol, carbamazepine, clobazam, clonazepam, diazepam, eslicarbazepine acetate, ethosuximide, felbamate, fosphenytoin sodium, gabapentin, lacosamide, lamotrigine, levetiracetam, lorazepam, mephenytoin, methlyphenobarbital, methosuximide, nitrazepam, oxcarbazepine, perampanel, piracetam, phenobarbital, phenytoin, pregabalin, primidone, retigabine, rufinamide, sodium valproate, stiripentol, tiagabine, topiramate, vigabatrin, zonisamide, everolimus, allopregnalone, Cenobamate, Fenfluramine hydrochloride, Ganaxolone, Immunoglobulin (human), ADX-71149, alprazolam, ataluren, buspirone hydrochloride, cannabidivarin, DP-VPA, naluzotan hydrochloride, PF-06372865, BM-MSCs (autologous), CPP-115, E-2730, huperzine A, radiprodil, SAGE-217, SAGE-516, [11C]UCB-J, AN2/AVex-73, AVL-5189, Alpha 1-24 corticotropin, CUR-1916, LY-3130481, MP-101, Metformin hydrochloride, SAGE-689, SF-0034 or TRP-005.

In some embodiments, the composition further comprises one or more of an additional anti-epileptic drug, optionally acetazolamide, brivaracetam, bromide, cannabidiol, carbamazepine, clobazam, clonazepam, diazepam, eslicarbazepine acetate, ethosuximide, felbamate, fosphenytoin sodium, gabapentin, lacosamide, lamotrigine, levetiracetam, lorazepam, mephenytoin, methlyphenobarbital, methosuximide, nitrazepam, oxcarbazepine, perampanel, piracetam, phenobarbital, phenytoin, pregabalin, primidone, retigabine, rufinamide, sodium valproate, stiripentol, tiagabine, topiramate, vigabatrin, or zonisamide, and a pharmaceutically acceptable carrier, optionally an excipient, lubricant, binder, disintegrant, solvent, solubilizing agent, suspending agent, isotonicity agent, buffer, soothing agent, preservative, antioxidant, colorant, and sweetening agent.

Aberrant cholesterol metabolism is implicated in epilepsy disorders/syndromes. In the brain, cholesterol is metabolized by cholesterol 24-hydroxylase (CH24H), which is specifically and constitutively expressed in neurons, to 24S-hydroxycholesterol (24HC). 24HC leaves the brain via lipoproteins and is excreted in bile.

Under normal conditions, extracellular glutamate is sequestered by glutamate transporters on neighboring astrocytes which require adequate cholesterol levels to efficiently maintain lipid raft structures in the astrocyte plasma membrane. Upon central nervous system (CNS) injury, CH24H is induced in reactive astrocytes and microglia. This leads to disruption in astrocytic glutamate homeostasis and a large increase in extracellular glutamate levels. As the CH24H enzyme converts cholesterol essential for the integrity of plasma membrane lipid rafts to 24HC, the circulating levels of 24HC increase, and may further contribute to underlying pathophysiological processes. Excessive extracellular glutamate and 24HC levels are thought to play major roles in excitotoxicity either through a sustained activation of the N-methyl-D-aspartate (NMDA) receptor channel or as a positive allosteric modulator of the receptor. The processes may be equally important in contributing to the enhanced glutamatergic activity observed in epilepsy disorders. Neurochemical processes, such as differential expression of genes and/or changes in neuroplasticity, occur in children at a different rate than in adults. This rate of change may represent an additional and nonspecific risk in children who are genetically predisposed to seizures. For example, the levels of 24HC can be up to 3 times higher in small children when compared to adults; it is, therefore, possible that the increased levels of 24HC in the children's brain are linked to more severe convulsions observed in rare epileptic syndromes. The compound (4-benzyl-4-hydroxypiperidin-1-yl) (2,4'-bipyridin-3-yl)methanone, shown below as Formula (I) is described in U.S. Pat. No. 8,648,079:

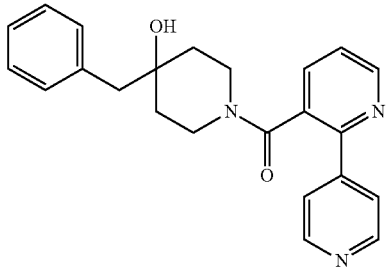

Formula (I)

The compound of Formula (I) is a CH24H inhibitor. Aspects of this disclosure relate to a method of treating an epileptic encephalopathy in a mammal (e.g., human, bovine, horse, dog, cat, monkey, mouse, rat; preferably human) in need thereof, comprising administering a composition comprising an effective amount of (4-benzyl-4-hydroxypiperidin-1-yl) (2,4'-bipyridin-3-yl)methanone or a pharmaceutically acceptable salt thereof to the mammal.

In some embodiments, the epileptic encephalopathy is selected from the group of Dravet syndrome (DS, severe myoclonic epilepsy in infancy), early myoclonic encephalopathy (Doose syndrome), Epilepsy with continuous spike-and-waves during slow-wave sleep (other than Landau-Kleffner syndrome), epilepsy of infancy with migrating focal seizures, Hypothalamic (gelastic) epilepsy, Landau-Kleffner syndrome, Lennox-Gastaut syndrome (LGS), Doose syndrome (myoclonic-astatic epilepsy), Myoclonic status in non-progressive encephalopathies, Ohtahara syndrome or early infantile epileptic encephalopathy, West syndrome, Glycine encephalopathy, 15q duplication syndrome (Dup15q) and Tuberous Sclerosis Complex (TSC) and seizures associated with mutations in CHD2, Cyclin-Dependent Kinase-Like 5 (CDKL5), SCN1A, SCN2A, SCN8A, ARX, KCNA1, KCNA2, KCNT1, KCNQ2, HCN1, PCDH19, GRIN1, GRIN2A and GRIN2B.

In some embodiments, the epileptic encephalopathy also means developmental and epileptic encephalopathy.

In some embodiments, the epileptic encephalopathy is selected from the group of Dravet syndrome (DS), Lennox-Gastaut syndrome (LGS), and Tuberous Sclerosis Complex (TSC).

As used herein, the term "treating" includes the prevention, reduction, and/or complete resolution of the symptoms associated with or the cause of the target indication and/or a lessening of severity of the condition.

As used herein, the term "effective amount" intends an amount effective to successfully achieve a particular biological effect. In the present case, the effective amount is an amount to effective to treat an epileptic encephalopathy. Suitable effective amounts may be determined according to methods well known in the art to determine single unit dosage and/or dose regimens.

In some embodiments, the contents of (4-benzyl-4-hydroxypiperidin-1-yl) (2,4'-bipyridin-3-yl)methanone or a pharmaceutically acceptable salt thereof in the present composition may vary from about 10% (w/w) to about 100% (w/w). Thus, the present composition may be (4-benzyl-4-hydroxypiperidin-1-yl) (2,4'-bipyridin-3-yl)methanone or a pharmaceutically acceptable salt thereof themselves.

In some embodiments, administering the effective amount of (4-benzyl-4-hydroxypiperidin-1-yl) (2,4'-bipyridin-3-yl)methanone or a pharmaceutically acceptable salt thereof results in (i) a reduction in the frequency of seizures in the mammal and/or (ii) a reduction in the plasma 24HC levels in the mammal.

In some embodiments, the effective amount of (4-benzyl-4-hydroxypiperidin-1-yl) (2,4'-bipyridin-3-yl)methanone or a pharmaceutically acceptable salt thereof is administered according to a dose regimen of either twice a day (BID) or once a day (QD) dosing.

The term "single unit dose" in this context refers to an effective amount provided in a single administration. Non-limiting examples of a suitable single unit doses for use in the claimed methods include at least about 0.8 mg/kg, between about 2 mg/kg and about 12 mg/kg, about 2 mg/kg, about 3 mg/kg, about 3.33 mg/kg, about 4 mg/kg, about 5 mg/kg, about 6 mg/kg, about 10 mg/kg, or about 12 mg/kg.

The term "dose regimen" in this context refers to an effective amount provided over a fixed number of administrations over a specified duration of time.

In some embodiments, the mammal is a human, optionally, an adult (18 years old or older), a juvenile (between 12 and 17 years old, endpoint inclusive), a child (between 2 and 11 years old, endpoint inclusive), an infant (between 1 month and 1 year of age, endpoint inclusive). It is appreciated that single unit doses may be tailored to the mammal being treated. For example, for humans, non-limiting exemplary single unit doses include less than about 1350 mg, between about 50 mg and about 800 mg (preferably between about 100 mg and about 800 mg), about 100 mg, about 150 mg, about 200 mg, about 300 mg, about 400 mg, about 600 mg or about 800 mg.

Suitable routes of administration and doses and formulations suited thereto are known in the art. Non-limiting examples of routes of administration relevant to the claimed methods include oral and parenteral (e.g., topical, rectal, or intravenous) routes. Examples of the dosage form suited for a particular route of administration include oral preparations such as tablet (including sugar-coated tablet, film-coated tablet, sublingual tablet, orally disintegrating tablet), capsules (including soft capsule, microcapsule), granule, powder, troche, syrup, emulsion, suspension, films (e.g., orally disintegrable films) and the like; and parenteral agents such as injection (e.g., subcutaneous injection, intravenous injection, intramuscular injection, intraperitoneal injection, drip infusion), external preparations (e.g., dermal preparation, ointment), suppository (e.g., rectal suppository, vaginal suppository), pellet, nasal preparation, pulmonary preparation (inhalant), eye drop and the like. Optionally, these preparations may be a release control preparation (e.g., sustained-release microcapsule) such as an immediate-release preparation or a sustained-release preparation.

In some embodiments, the effective amount of (4-benzyl-4-hydroxypiperidin-1-yl) (2,4'-bipyridin-3-yl)methanone or a pharmaceutically acceptable salt thereof is administered orally.

In some embodiments, the method further comprises administering an additional composition comprising an effective amount of an additional anti-epileptic drug. In other embodiments, the composition comprising the effective amount of (4-benzyl-4-hydroxypiperidin-1-yl) (2,4'-bipyridin-3-yl)methanone or a pharmaceutically acceptable salt thereof further comprises one or more of an additional anti-epileptic drug.

Non-limiting examples of additional anti-epileptic drugs include acetazolamide, brivaracetam, bromide, cannabidiol, carbamazepine, clobazam, clonazepam, diazepam, eslicarbazepine acetate, ethosuximide, felbamate, fosphenytoin sodium, gabapentin, lacosamide, lamotrigine, levetiracetam, lorazepam, mephenytoin, methylphenobarbital, methosuximide, nitrazepam, oxcarbazepine, perampanel, piracetam, phenobarbital, phenytoin, pregabalin, primidone, retigabine, rufinamide, sodium valproate, stiripentol, tiagabine, topiramate, vigabatrin, and zonisamide.

In some embodiments, the composition comprising the effective amount of (4-benzyl-4-hydroxypiperidin-1-yl) (2,4'-bipyridin-3-yl)methanone or a pharmaceutically acceptable salt thereof further comprises a pharmaceutically acceptable carrier.

As used herein, the term "pharmaceutically acceptable carrier" intends one or more organic or inorganic carrier substances conventionally used in the formulation of pharmaceutical compositions.

Suitable pharmaceutically acceptable carriers can be determined by methods well known in the art, e.g. excipients, lubricants, binders and disintegrants; solvents, solubilizing agents, suspending agents, isotonicity agents, buffers, and soothing agents; and/or preparation additives such as preservatives, antioxidants, colorants, and sweetening agents.

In some embodiments, the pharmaceutically acceptable carrier is an excipient, lubricant, binder, disintegrant, solvent, solubilizing agent, suspending agent, isotonicity agent, buffer, soothing agent, preservative, antioxidant, colorant, and sweetening agent.

Non-limiting examples of such suitable pharmaceutically acceptable carriers include:

for an excipient: lactose, sucrose, D-mannitol, D-sorbitol, starch, gelatinated starch, dextrin, crystalline cellulose, low-substituted hydroxypropylcellulose, sodium carboxymethylcellulose, gum arabic, pullulan, light anhydrous silicic acid, synthesis aluminum silicate and magnesium alumino metasilicate;

for a lubricant: magnesium stearate, calcium stearate, talc and colloidal silica;

for a binder: gelatinated starch, sucrose, gelatin, gum arabic, methylcellulose, carboxymethylcellulose, sodium carboxymethylcellulose, crystalline cellulose, sucrose, D-mannitol, trehalose, dextrin, pullulan, hydroxypropylcellulose, hydroxypropylmethylcellulose and polyvinylpyrrolidone;

for a disintegrant: lactose, sucrose, starch, carboxymethylcellulose, calcium carboxymethylcellulose, croscarmellose sodium, sodium carboxymethyl starch, light anhydrous silicic acid and low-substituted hydroxypropylcellulose;

for a solvent: water, physiological brine, Ringer's solution, alcohol, propylene glycol, polyethylene glycol, sesame oil, corn oil, olive oil and cottonseed oil;

for a solubilizing agent: polyethylene glycol, propylene glycol, D-mannitol, trehalose, benzyl benzoate, ethanol, trisaminomethane, cholesterol, triethanolamine, sodium carbonate, sodium citrate, sodium salicylate and sodium acetate;

for a suspending agent: surfactants such as stearyltriethanolamine, sodium lauryl sulfate, lauryl aminopropionate, lecithin, benzalkonium chloride, benzethonium chloride, and glycerol monostearate; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose and the like; polysorbates, and polyoxyethylene hydrogenated castor oil;

for an isotonicity agent: sodium chloride, glycerol, D-mannitol, D-sorbitol and glucose;

for a buffer: phosphate, acetate, carbonate, and citrate;

for a soothing agent: benzyl alcohol;

for a preservative: p-oxybenzoates, chlorobutanol, benzyl alcohol, phenethyl alcohol, dehydroacetic acid, and sorbic acid;

for an antioxidant: sulfite and ascorbate;

for a colorant: aqueous water-soluble food tar colors (e.g., food colors such as Food Color Red Nos. 2 and 3, Food Color Yellow Nos. 4 and 5, Food Color Blue Nos. 1 and 2 and the like), water insoluble lake dyes (e.g., aluminum salt of the above-mentioned water-soluble food tar color), and natural dyes (e.g., β-carotene, chlorophyll, ferric oxide red); and for a sweetening agent: saccharin sodium, dipotassium glycyrrhizinate, aspartame, and stevia.

Examples of a metabolite of (4-benzyl-4-hydroxypiperidin-1-yl) (2,4'-bipyridin-3-yl)methanone include a compound shown below:

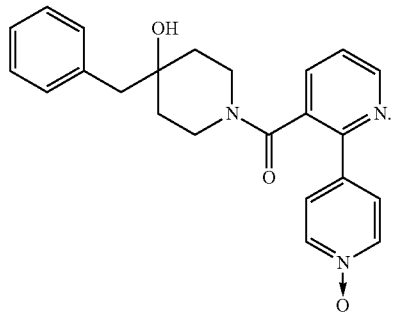 [SMILES: O=C(c1cccnc1-c1cc[n+]([O-])cc1)N1CCC(O)(Cc2ccccc2)CC1]

The invention is further illustrated by, though in no way limited to, the following examples.

EXAMPLES

Example 1—Safety and Efficacy Studies

Four clinical studies including a single-rising dose (SRD) first-in-human study, a single-dose positron emission tomography (PET) target occupancy study, a multiple-rising dose (MRD) study, and a single-dose relative bioavailability (BA) and food-effect study were conducted.

The pharmacokinetics (PK) and pharmacodynamics (PD) of (4-benzyl-4-hydroxypiperidin-1-yl) (2,4'-bipyridin-3-yl)methanone were characterized in these studies.

The results of the PET study provided clinical evidence of dose-dependent decreases in plasma 24HC concentrations and PET occupancy measurements that were dose- and time-dependent and correlated with circulating levels of 24HC. Tables 1-1 and 1-2 show the results of safety evaluation.

TABLE 1-1

| Reporting Groups (Time Frame 30 Days) | |
|---|---|
| Cohorts 1-6: Placebo | Placebo-matching solution, orally, once, on Day 1. |
| Cohort 1: 15 mg of (4-benzyl-4-hydroxypiperidin-1-yl)(2,4'-bipyridin-3-yl)methanone | (4-benzyl-4-hydroxypiperidin-1-yl)(2,4'-bipyridin-3-yl)methanone 15 mg solution, orally, once, on Day 1. |

TABLE 1-1-continued

Reporting Groups (Time Frame 30 Days)

| | |
|---|---|
| Cohorts 1-6: Placebo | Placebo-matching solution, orally, once, on Day 1. |
| Cohort 2: 50 mg of (4-benzyl-4-hydroxypiperidin-1-yl)(2,4'-bipyridin-3-yl)methanone | (4-benzyl-4-hydroxypiperidin-1-yl)(2,4'-bipyridin-3-yl)methanone 50 mg solution, orally, once, on Day 1. |
| Cohort 3: 200 mg of (4-benzyl-4-hydroxypiperidin-1-yl)(2,4'-bipyridin-3-yl)methanone | (4-benzyl-4-hydroxypiperidin-1-yl)(2,4'-bipyridin-3-yl)methanone 200 mg solution, orally, once, on Day 1. |
| Cohort 4: 600 mg of (4-benzyl-4-hydroxypiperidin-1-yl)(2,4'-bipyridin-3-yl)methanone | (4-benzyl-4-hydroxypiperidin-1-yl)(2,4'-bipyridin-3-yl)methanone 600 mg solution, orally, once, on Day 1. |
| Cohort 5: 900 mg of (4-benzyl-4-hydroxypiperidin-1-yl)(2,4'-bipyridin-3-yl)methanone | (4-benzyl-4-hydroxypiperidin-1-yl)(2,4'-bipyridin-3-yl)methanone 900 mg solution, orally, once, on Day 1. |
| Cohort 6: 1350 mg of (4-benzyl-4-hydroxypiperidin-1-yl)(2,4'-bipyridin-3-yl)methanone | (4-benzyl-4-hydroxypiperidin-1-yl)(2,4'-bipyridin-3-yl)methanone 1350 mg solution, orally, once, on Day 1. |

TABLE 1-2

Serious Adverse Events

| | Total, Serious Adverse Events # participants affected/at risk |
|---|---|
| Cohorts 1-6: Placebo | 0/12 (0.00%) |
| Cohort 1: 15 mg | 0/6 (0.00%) |
| Cohort 2: 50 mg | 0/6 (0.00%) |
| Cohort 3: 200 mg | 0/6 (0.00%) |
| Cohort 4: 600 mg | 0/6 (0.00%) |
| Cohort 5: 900 mg | 0/6 (0.00%) |
| Cohort 6: 1350 mg | 0/6 (0.00%) |

No serious pretreatment events or post treatment adverse events were reported.

The safety results from these studies show that doses up to 1350 mg single dose is generally safe and well tolerated in healthy male and female subjects (Tables 1-1 and 1-2).

A further safety and tolerability study is being conducted to examine the safety, tolerability, pharmacokinetics (PK), and pharmacodynamics (PD) of (4-benzyl-4-hydroxypiperidin-1-yl) (2,4'-bipyridin-3-yl)methanone as an adjunctive therapy in human subjects with epileptic encephalopathies.

The study examines adult subjects between the ages of 18 and 65 with epileptic encephalopathies, including but not limited to Dravet Syndrome (DS), Lennox-Gastaut Syndrome (LGS), and Tuberous Sclerosis Complex (TSC), demonstrating countable motor seizures (i.e., ≥2 per month during the past 3 months).

The study enrolls 20 subjects. The study examines the safety and tolerability of 100 mg, 200 mg and 300 mg BID doses vs. placebo in patients with epileptic encephalopathies. Efficacy (seizure count using a daily seizure diary completed by the patients or their care giver), PK and 24HC levels are also collected in the study.

At the Screening Visit, informed consent and/or assent (if applicable) is obtained from the subjects and/or subjects' legally acceptable representative. Subjects undergo screening procedures to assess study eligibility in accordance with the study entry criteria. At this Screening Visit and at subsequent visits, subjects and/or subjects' caregivers are provided with a seizure diary and are instructed to record seizure data on a daily basis starting at Baseline and throughout the study. The seizure diary data collected during a 4-week period is used as the baseline seizure data for endpoint analysis. PD blood sample collection for measurement of baseline plasma 24HC levels is also done at the Screening Visit. The 4-week Baseline Period seizure diary recording can begin as soon as informed consent has been signed. At the end of the 4-week Baseline Period and after confirmation of eligibility, subjects return to the clinic on Day 1 in Part 1 for randomization. If a subject does not meet the eligibility criteria during the Screening/Baseline Period, the subject is discontinued from the study.

The study consists of 2 parts:

Part 1 is a randomized double-blind part consisting of 3 periods: a screening/baseline period (4-6 weeks), titration period (20 days), and maintenance period (10 days). The target final dose of 300 mg BID is reached after a 20-day titration period.

Part 2 is an open-label continuation part consisting of 4 periods: a titration period (10 days), maintenance period (44 days), de-escalation period (3-6 days) and follow-up period (30 days).

Part 1 of the study is designed to investigate the safety, tolerability, PK, and PD in adult subjects with developmental and/or epileptic encephalopathies in a double-blind manner. Efficacy of (4-benzyl-4-hydroxypiperidin-1-yl) (2,4'-bipyridin-3-yl)methanone on seizure frequency is investigated in an exploratory manner. A total of 20 adult subjects who demonstrate ≥1 bilateral motor seizure (drop seizures, tonic-clonic, tonic, bilateral clonic, atonic, myoclonic-atonic, myoclonic-tonic-clonic, focal seizures with bilateral hyperkinetic motor features) during the 4-week Baseline Period is randomly assigned on Day 1 to receive (4-benzyl-4-hydroxypiperidin-1-yl) (2,4'-bipyridin-3-yl)methanone (n=16) or matching placebo (n=4) twice daily (BID) orally for 30 days during the Double-Blind Treatment Period. Subjects initiate IP (investigational product); (4-benzyl-4-hydroxypiperidin-1-yl) (2,4'-bipyridin-3-yl)methanone or placebo) at 100 mg BID from Days 1 through 10. Subjects who cannot tolerate the 100 mg BID dosing are withdrawn from the study. On Day 11, subjects return to the clinic and the IP dose is increased to 200 mg BID; this dose level is maintained from Days 11 through 20 but is reduced to 100 mg BID in subjects who cannot tolerate the 200 mg BID dose or demonstrate safety concerns, based on the investigator's judgement and in consultation with the subject's caregiver, when applicable. On Day 21, subjects return to the clinic; at this visit, the investigator reviews the subject's safety data and discusses the benefit-risk assessment with the subject or subject's legally acceptable representative before proceeding to increase the dose from 200 mg BID to 300 mg BID, and this dose level is maintained from Days 21 through 30. The dose may be reduced to 200 mg BID in subjects who cannot tolerate the 300 mg BID dose or demonstrate safety concerns, as described above. Subjects for whom the dose was reduced to a lower dose level stay on that dose level until the end of the Double-Blind Treatment Period.

Three days after each dose up-titration or de-escalation, subjects are contacted by phone to monitor study drug compliance, concomitant medication use, and AEs. Any change in dose is documented in the subject's clinic chart and the subject's caregiver is advised to note the same in the dosing card.

On Day 1, PK, PD, anti-epileptic drug, and optional PGx blood samples will be collected before the morning dose of study drug. PK and PD blood samples are also collected at 1, 3, and 5 hours after the morning dose on Day 1. On Day 11 and Day 21, PK and PD blood samples (before and approximately 1 hour after morning dose), an anti-epileptic drug blood sample (before morning dose), and seizure diary data are collected. Subjects who are unwilling to continue into Part 2 of the study proceed directly to the Final Visit, including dose de-escalation, as appropriate, followed by the 30-day Follow-up Period.

Part 2 of the study is designed to investigate the safety, tolerability, PK, and PD of (4-benzyl-4-hydroxypiperidin-1-yl) (2,4'-bipyridin-3-yl)methanone in adult subjects with-epileptic encephalopathies in an open-label manner. All subjects who complete the Double-Blind Treatment Period in Part 1 have the option to continue directly into the Open-Label Treatment Period in Part 2. Because some subjects may enter Part 2 after receiving placebo and others (4-benzyl-4-hydroxypiperidin-1-yl) (2,4'-bipyridin-3-yl) methanone up to 300 mg BID and to maintain the study blind, all subjects start on (4-benzyl-4-hydroxypiperidin-1-yl) (2,4'-bipyridin-3-yl)methanone 200 mg BID at the start of Part 2. On Day 31, subjects return to the clinic and receive (4-benzyl-4-hydroxypiperidin-1-yl) (2,4'-bipyridin-3-yl) methanone 200 mg BID from Days 31 to 40 but may be reduced to 100 mg BID in subjects who cannot tolerate the 200 mg BID dose or demonstrate safety concerns, based on the investigator's judgement and in consultation with the subject's caregiver, when applicable. Subjects who cannot tolerate the 100 mg BID dose or demonstrate safety concerns, based on the investigator's judgement and in consultation with the subject's caregiver, is discontinued from the study. On Day 41, subjects return to the clinic; at this visit, the investigator review the subject's safety data and discuss the benefit-risk assessment with the subject or subject's legally acceptable representative before proceeding to increase the dose from 200 mg BID to 300 mg BID, and this dose level is maintained until the Final Visit for the dose de-escalation phase. Subjects' dose may be increased or decreased before Day 41 based on clinical condition (i.e., increasing seizures) and investigator judgment. This dose may be reduced to 200 mg BID in subjects who cannot tolerate the 300 mg BID dose or demonstrate safety concerns, as described above. Subjects for whom the dose was reduced to a lower dose level stay on that dose level until the Final Visit for the dose de-escalation phase. Three days after each dose up-titration or de-escalation, subjects are contacted by phone to monitor study drug compliance, concomitant medication use, and adverse effects. Any change in dose is documented in the subject's clinic chart and the subject's caregiver is advised to note the same in the dosing card.

On Day 31, PK, PD, anti-epileptic drug, and PGx (if collected on Day 1) blood samples are collected before the morning dose of study drug and seizure data are also collected. On Day 41, PK, PD, and anti-epileptic drug blood samples are collected before the morning dose of study drug and seizure data are also collected.

On Day 85, subjects return to the clinic for the Final Visit and enter the 3- or 6-day de-escalation phase. At this visit, PK, PD, and anti-epileptic drug blood samples are collected before the morning dose of study drug and seizure data are also collected. Subjects then enter the dose de-escalation phase and are instructed to follow the applicable de-escalation dosing schedule outlined below:

For subjects on 300 mg BID during the maintenance phase, the dose is de-escalated to 200 mg BID for 3 days (Days 85-87) and subsequently to 100 mg BID for 3 days (Days 88-90).

For subjects on 200 mg BID during the maintenance phase, the dose is de-escalated to 100 mg BID for 3 days (Days 85-87).

For subjects on 100 mg BID during the maintenance phase, there is no de-escalation and the dose is discontinued on Day 85.

Immediately after the last dose is the 30-day Follow-up Period comprised of a Follow-up Phone Call on Day 91 and a Follow-up Visit on Day 121. At the Follow-up Visit, subjects return to the clinic for study procedures including PD and AED blood sample collection.

In Parts 1 and 2, subjects are instructed to not take their morning dose of study drug or concomitant anti-epileptic drugs on the days of scheduled study visits to facilitate collection of the predose PK, PD, anti-epileptic drug, and optional PGx blood samples. The morning dose of study drug and concomitant anti-epileptic drug are administered in the clinic on these study days after laboratory samples are collected.

For subjects who are not able to come for the visit during the morning hours, they should be instructed to take their morning dose, as usual, and come to the study site during the afternoon hours, as feasible for the subject. While in the clinic, the site should attempt to obtain 2 PK samples, separated by 1-2 hours, if possible. Hours since the last dose of the study medication must be recorded in the eCRF upon collection of the PK sample(s).

Seizure data are recorded daily in the seizure diary by each subject and/or subjects' caregiver throughout the Screening/Baseline Period up until the Follow-up Visit on Day 121 and is collected from the diary at each visit.

Example 2 Pre-Clinical Seizure Model Data

The following Example provides data from a heterozygous deletion of a Scn1a mouse model (Scn1a+/−mice) of Dravet syndrome, a developmental epileptic encephalopathy subtype. Myoclonic and generalized tonic-clonic seizures are observed, which correlate to symptoms in humans. Therefore, (4-benzyl-4-hydroxypiperidin-1-yl) (2,4'-bipyridin-3-yl)methanone was tested in Scn1a+/−mice for its potential effects on seizure. At 17-18 days after birth, mice were weaned and started on treatment either with control chow or chow containing (4-benzyl-4-hydroxypiperidin-1-yl) (2,4'-bipyridin-3-yl)methanone 0.02% (w/w) for 2 weeks. Spontaneous seizures were continuously monitored. The seizure free rate during the study period for the control group was 23.9%. In contrast, the seizure free rate during the study period for the group treated with (4-benzyl-4-hydroxypiperidin-1-yl) (2,4'-bipyridin-3-yl)methanone was 91.7%. These results support the use of (4-benzyl-4-hydroxypiperidin-1-yl) (2,4'-bipyridin-3-yl)methanone to treat epileptic encephalopathies.

Example 3 Study in Pediatric Patients (Aged ≥2 and ≤17 Years) with Dravet Syndrome and Lennox Gastaut Syndrome This is a multicenter, randomized, double-blind, placebo-controlled, parallel-group, study in pediatric patients (aged ≥2 and ≤17 years) with Dravet syndrome and Lennox Gastaut syndrome demonstrating ≥3 convulsive or ≥4 drop seizures per month during the 3 months immediately prior to Screening (based on historic information) and ≥3 convulsive or ≥4 drop seizures during a minimum of 4 weeks during the prospective Baseline Period (based on the seizure diary records). Convulsive seizures include generalized tonic-clonic, focal to bilateral tonic-clonic with impaired awareness, hemi-clonic and simultaneous bilateral clonic (generalized clonic) seizures. Drop seizures are defined as involving the entire body, trunk, or head that leads to a fall, injury, slumping in a chair, or head hitting a surface, or that could have led to a fall or injury, depending on the position of the patient at the time of the seizure or spell. Examples of seizures causing drop include, but are not limited to, atonic, clonic, and tonic seizures.

Approximately 126 patients will be randomized to ensure 112 evaluable patients. Randomization will be stratified by 2 categories: patients with Dravet syndrome with convulsive seizures and patients with Lennox Gastaut Syndrome (LGS) with drop seizures. Stratification will be performed to ensure balance of treatments within each stratum.

The study will begin with a phased enrollment based on age. Patients aged ≥9 years will be enrolled first, prior to open enrollment in the study, for assessment of safety. The independent Data Monitoring Committee (iDMC) will review the adverse event (AE) profile of the first 20 patients aged ≥9 years completing treatment, prior to recommending treatment for patients aged <9 years.

This study consists of 2 main periods:
4- to 6-week Screening/Baseline Period
14-week Treatment Period
2-week Titration Period
12-week Maintenance Period The Treatment Period consists of Titration Period and Maintenance Period.

Dravet syndrome patients who have had on average ≥3 convulsive or LGS patients who have had on average ≥4 drop seizures per month during the 3 months immediately prior to Screening (based on the historical information) and ≥3 convulsive or ≥4 drop seizures during a minimum of 4 weeks during the Baseline Period (based on the seizure diary records) will be eligible for entry into the study. The patients who meet the entry criteria will be randomized in a 1:1 ratio to double-blind treatment with (4-benzyl-4-hydroxypiperidin-1-yl) (2,4'-bipyridin-3-yl)methanone or matching placebo for the 14-week Treatment Period (2-week Titration Period and 12-week Maintenance Period).

Formulation Example

For (4-benzyl-4-hydroxypiperidin-1-yl) (2,4'-bipyridin-3-yl)methanone, the formulation (film coating tablet) was produced in line with the following specification (Table 2).

TABLE 2

| | Components | Quantity per Tablet(mg) 20 mg |
|---|---|---|
| Core Tablet (Internal granules) | (4-benzyl-4-hydroxypiperidin-1-yl)(2,4'-bipyridin-3-yl)methanone | 20 |
| | Microcrystalline cellulose (PH101) | 1.5 |
| | Low-Substituted Hydroxypropyl Cellulose (L-HPC 21) | 1.25 |
| | Hydroxypropyl Cellulose | 0.75 |
| (External granules) | Low-Substituted Hydroxypropyl Cellulose (L-HPC 21) | 1.25 |
| | Magnesium Stearate | 0.25 |

TABLE 2-continued

| | Components | Quantity per Tablet(mg) 20 mg |
|---|---|---|
| Coating Solution | (OPADRY Red 03F45081) | 0.508 |
| | (OPADRY Yellow 03F42240) | 0.508 |
| | Hypromellose 2910[1] | (0.75) |
| | Polyethylene Glycol 8000[1] | (0.167) |
| | Titanium Dioxide[1] | (0.083) |
| | Ferric Oxide, Red[1] | (0.008) |
| | Ferric Oxide, Yellow[1] | (0.008) |
| | Total | 26.016 |

[1]These ingredients are components of OPADRY (registered trademark) Red 03F45081 and OPADRY (registered trademark) Yellow 03F42240 (premixed coating materials).

INDUSTRIAL APPLICABILITY

According to the present invention, an efficient method of treating an epileptic encephalopathy in a mammal in need thereof, comprising administering a composition comprising an effective amount of (4-benzyl-4-hydroxypiperidin-1-yl) (2,4'-bipyridin-3-yl)methanone or a pharmaceutically acceptable salt thereof to the mammal can be provided.

This application is based on patent application No. 62/553,070 filed on Aug. 31, 2017 in the US, the contents of which are encompassed in full herein.

The invention claimed is:

1. A method of treating an epileptic encephalopathy in a mammal in need thereof, comprising administering a composition comprising an effective amount of (4-benzyl-4-hydroxypiperidin-1-yl) (2,4'-bipyridin-3-yl) methanone or a pharmaceutically acceptable salt thereof to the mammal.

2. The method of claim 1, wherein the epileptic encephalopathy is selected from the group of Dravet syndrome, Early myoclonic encephalopathy, Epilepsy with continuous spike-and-waves during slow-wave sleep other than Landau-Kleffner syndrome, epilepsy of infancy with migrating focal seizures, Hypothalamic epilepsy, Landau-Kleffner syndrome, Lennox-Gastaut syndrome, Doose syndrome, Myoclonic status in non-progressive encephalopathies, Ohtahara syndrome or early infantile epileptic encephalopathy, West syndrome, Glycine encephalopathy, 15q duplication syndrome and Tuberous Sclerosis Complex and seizures associated with mutations in CHD2, Cyclin-Dependent Kinase-Like 5, SCN1A, SCN2A, SCN8A, ARX, KCNA1, KCNA2, KCNT1, KCNQ2, HCN1, PCDH19, GRIN1, GRIN2A and GRIN2B.

3. The method of claim 1, wherein the epileptic encephalopathy is selected from the group of Dravet syndrome, Lennox-Gastaut syndrome, Tuberous Sclerosis Complex and seizures associated with mutations in CHD2, Cyclin-Dependent Kinase-Like 5, SCN1A, SCN2A, SCN8A, ARX, KCNA1, KCNA2, KCNT1, KCNQ2, HCN1, PCDH19, GRIN1, GRIN2A and GRIN2B.

4. The method of claim 1, wherein administering the effective amount of (4-benzyl-4-hydroxypiperidin-1-yl) (2,4'-bipyridin-3-yl)methanone or a pharmaceutically acceptable salt thereof results in (i) a reduction in the frequency of seizures in the mammal and/or (ii) a reduction in the plasma 24HC levels in the mammal.

5. The method of claim 1, wherein the effective amount of (4-benzyl-4-hydroxypiperidin-1-yl) (2,4'-bipyridin-3-yl) methanone or a pharmaceutically acceptable salt thereof is administered orally.

6. The method of claim 1, wherein the effective amount of (4-benzyl-4-hydroxypiperidin-1-yl) (2,4'-bipyridin-3-yl)

methanone or a pharmaceutically acceptable salt thereof is administered as a single unit dose.

7. The method of claim 6, wherein the single unit dose is at least about 0.8 mg/kg.

8. The method of claim 6, wherein the single unit dose is between about 2 mg/kg and about 12 mg/kg.

9. The method of claim 6, wherein the single unit dose is selected from the consisting of about 0.8 mg/kg, about 2 mg/kg, about 3 mg/kg, about 3.33 mg/kg, about 4 mg/kg, about 5 mg/kg, about 6 mg/kg, about 10 mg/kg, and about 12 mg/kg.

10. The method of claim 1, wherein the effective amount of (4-benzyl-4-hydroxypiperidin-1-yl) (2,4'-bipyridin-3-yl)methanone or a pharmaceutically acceptable salt thereof is administered according to a dose regimen of either twice a day or once a day dosing.

11. The method of claim 1, wherein the mammal is a human.

12. The method of claim 11, wherein the human is an adult, a juvenile, a child, or an infant.

13. The method of claim 11, wherein the effective amount of (4-benzyl-4-hydroxypiperidin-1-yl) (2,4'-bipyridin-3-yl)methanone or a pharmaceutically acceptable salt thereof is administered as a single unit dose.

14. The method of claim 13, wherein the single unit dose is less than about 1350 mg.

15. The method of claim 13, wherein the single unit dose is between about 50 mg and about 800 mg.

16. The method of claim 13, wherein the single unit dose is between about 100 mg and about 800 mg.

17. The method of claim 13, wherein the single unit dose is selected from the group consisting of about 100 mg, about 150 mg, about 200 mg, about 300 mg, about 400 mg, about 600 mg and about 800 mg.

18. The method of claim 11, wherein the effective amount of (4-benzyl-4-hydroxypiperidin-1-yl) (2,4'-bipyridin-3-yl)methanone or a pharmaceutically acceptable salt thereof is administered twice a day.

19. The method of claim 18, wherein (4-benzyl-4-hydroxypiperidin-1-yl) (2,4'-bipyridin-3-yl)methanone is administered at the daily dose of between about 100 mg and about 800 mg.

20. The method of claim 18, wherein (4-benzyl-4-hydroxypiperidin-1-yl) (2,4'-bipyridin-3-yl)methanone is administered according to a dose regimen selected from the group consisting of about 50 mg twice a day, about 100 mg twice a day, about 200 mg twice a day, about 300 mg twice a day and about 400 mg twice a day.

21. The method of claim 18, wherein (4-benzyl-4-hydroxypiperidin-1-yl) (2,4'-bipyridin-3-yl)methanone is administered according to a dose regimen of about 400 mg twice a day.

22. The method of claim 1, further comprising administering an additional composition comprising an effective amount of an additional anti-epileptic drug.

23. The method of claim 22, wherein the additional anti-epileptic drug is selected from the group of acetazolamide, brivaracetam, bromide, cannabidiol, carbamazepine, clobazam, clonazepam, diazepam, eslicarbazepine acetate, ethosuximide, felbamate, fosphenytoin sodium, gabapentin, lacosamide, lamotrigine, levetiracetam, lorazepam, mephenytoin, methlyphenobarbital, methosuximide, nitrazepam, oxcarbazepine, perampanel, piracetam, phenobarbital, phenytoin, pregabalin, primidone, retigabine, rufinamide, sodium valproate, stiripentol, tiagabine, topiramate, fenfluramine, vigabatrin, and zonisamide.

24. The method of claim 1, wherein the composition further comprises one or more of an additional anti-epileptic drug and a pharmaceutically acceptable carrier.

25. The method of claim 24, wherein the additional anti-epileptic drug is selected from the group of acetazolamide, brivaracetam, bromide, cannabidiol, carbamazepine, clobazam, clonazepam, diazepam, eslicarbazepine acetate, ethosuximide, felbamate, fosphenytoin sodium, gabapentin, lacosamide, lamotrigine, levetiracetam, lorazepam, mephenytoin, methlyphenobarbital, methosuximide, nitrazepam, oxcarbazepine, perampanel, piracetam, phenobarbital, phenytoin, pregabalin, primidone, retigabine, rufinamide, sodium valproate, stiripentol, tiagabine, topiramate, vigabatrin, and zonisamide.

* * * * *